US005486621A

United States Patent [19]
Phillion et al.

[11] Patent Number: 5,486,621
[45] Date of Patent: Jan. 23, 1996

[54] FUNGICIDES FOR THE CONTROL OF TAKE-ALL DISEASE OF PLANTS

[75] Inventors: Dennis Phillion, St. Charles; Sai C. Wong, Chesterfield; Barry Shortt, New Melle, all of Mo.

[73] Assignee: Monsanto Company, St. Louis, Mo.

[21] Appl. No.: 356,770

[22] Filed: Dec. 15, 1994

[51] Int. Cl.$^6$ .......................... C07D 333/72; A01N 43/10
[52] U.S. Cl. ................... 549/4; 514/448; 514/438
[58] Field of Search ..................... 549/4, 72, 487; 514/448, 471, 438

[56] References Cited

U.S. PATENT DOCUMENTS

| | | | |
|---|---|---|---|
| 4,097,265 | 6/1978 | Kobzina | 71/90 |
| 4,102,668 | 7/1978 | Foery et al. | 71/90 |
| 4,228,165 | 10/1980 | Ogata et al. | 424/248.5 |
| 4,248,869 | 2/1981 | Ogata et al. | 424/248.5 |
| 4,448,105 | 11/1984 | Shepherd et al. | 424/248.54 |
| 4,997,836 | 3/1991 | Sugihara et al. | 514/253 |
| 4,999,381 | 3/1991 | Crowley et al. | 514/618 |
| 5,053,073 | 10/1991 | Anthony et al. | 549/59 |
| 5,201,934 | 4/1993 | Muenster et al. | 504/289 |
| 5,286,862 | 2/1994 | Schubert | 546/14 |
| 5,369,124 | 11/1994 | Elbe et al. | 514/448 |

FOREIGN PATENT DOCUMENTS

| | | |
|---|---|---|
| 0619297 | 10/1994 | European Pat. Off. |
| 63-284186 | 11/1988 | Japan . |
| 93/07751 | 4/1993 | WIPO . |

OTHER PUBLICATIONS

Carpenter, et al. J. Org. Chemistry, 50(22):4362–4368, 1985.
Doadt, et al. Tetrahedron Letters, 26(9):1149–1152, 1985.
Fitt, J. J. et al. J. Org. Chemistry, 41(25):4029–4031, 1976.
Nishimoto, et al. Chem. Abstracts, 101(19) 170383 y, 1984.
Takahashi, et al., Quant.Struct.–Act. Relat. 6(1):17–21, 1987.
White, et al, Pesticide Biochemistry and Physiol., 25:188–204, 1986.

*Primary Examiner*—Richard L. Raymond
*Assistant Examiner*—Deborah Lambkin
*Attorney, Agent, or Firm*—Joan Thierstein; Jon Beusen

[57] ABSTRACT

This invention relates to 4,5-dimethyl-N-2-propenyl-2-(trimethylsilyl)-3-thiophenecarboxamide, a method for the control of Take-All disease (Gaeumannomyces species) in plants by the use of this compound, and to fungicidal compostions for carrying out the method.

7 Claims, No Drawings

FUNGICIDES FOR THE CONTROL OF TAKE-ALL DISEASE OF PLANTS

FIELD OF THE INVENTION

This invention relates to a certain novel substituted thiophene, a method for the control of Take-All disease in plants, particularly cereals, by the use of the compound, and fungicidal compostions for carrying out the method.

BACKGROUND OF THE INVENTION

Take-All disease is a serious problem in the production of cereals, particularly wheat and barley. It is caused by the soil-borne fungus *Gaeumannomyces graminis* (Gg). The fungus infects the roots of the plant, and grows throughout the root tissue, causing a black rot. The growth of the fungus in the roots and lower stem prevents the plant from obtaining sufficient water and/or nutrients from the soil, and is manifested as poor plant vigor and, in severe instances of disease, by the formation of "whiteheads," which are barren or contain few, shriveled grains. Yield losses result. Gaeumannomyces species also infect other cereal crops, for example, rice and oats; and turf.

Currently the primary means of avoiding crop loss due to infestation of the soft by Gg has been to rotate the crop grown to one which is resistant to Gg. However, in areas where the primary crops are cereals, rotation is not a desirable practice, and an effective control agent is greatly desired.

The international patent application PCT/US92/08633 discloses a broad scope of compounds effective against Take-all disease. The present invention is a selected compound having superior and unexpected effectiveness against the present disease.

It is an object of the present invention to provide a compound that provides superior and unexpected control of the growth of Gg in the soft to reduce crop loss. It is a further object of this invention to provide an effective method for superior and unexpected control of Take-all disease in plants. It is still a further object of this invention to provide fungicidal compositions that may be used for superior and unexpected control of Take-All disease.

These and other objects of the invention will be apparent to those skilled in this art from the following detailed description of a preferred embodiment of the invention.

SUMMARY OF THE INVENTION

The present invention provides for the compound 4,5-dimethyl-N-2-propenyl-2-(trimethylsilyl)-3-thiophenecarboxamide, hereinafter designated compound I.

The present invention provides a method of controlling disease caused by Gaeumannomyces species in plants comprising applying to the seed, or the soil, a fungicidally effective amount of the fungicide of compound I.

The invention also provides fungicidal compositions comprising a fungicidally effective amount of compound I and an agronomically acceptable carder useful in said method.

A preferred embodiment of the present invention is compound I, as well as a fungicidal composition and fungicidal method of use.

DETAILED DESCRIPTION OF THE INVENTION

Compound I may be prepared by methods known to those of ordinary skill in the art, for example, the international patent application PCTT/US92/08633. Compound I can also be prepared as shown below in Example 1.

EXAMPLE 1 STEP 1

Preparation of
2-amino-4,5-dimethyl-3-thiophenecarboxylic acid,
ethyl ester

| Chemicals | Mol. Wt | Weight | Volume | Moles |
| --- | --- | --- | --- | --- |
| 2-Butanone | 72.11 | 1800 g | 2236 mL | 25.0 |
| Ethyl Cyanoacetate | 113.12 | 2833 g | 2665 mL | 25.0 |
| Sulfur | 32.06 | 800 g | — | 25.0 |
| Diethylamine | 73.14 | 1829 g | 2586 mL | 25.0 |
| Ethanol | 4.3 Liters | | | |

Under an $N_2$ purge in a clean, dry 22 L RB flask is mixed 2-butanone, ethyl cyanoacetate and ethanol. Powdered sulfur is added and stirred well. Diethylamine is then added in a rapid continuous stream into the vessel. Stirring is continued and the temperature is raised to above 45°–50° C. for a two hour minimum. When the heating cycle is completed, the dark red brown solution is pumped into a stirring mixture of ice and water (about 25 L). After the precipitate has hardened well, the slurry is filtered, pulled free of filtrate and then air dried on the filter. After the solid is dry, the cake is triturated with hexane until the filtrate is nearly colorless. Then the solids are dried under a nitrogen stream. The yield is 3050 g (about 60%) of the sandy red brown product with >92% area by GC. $^1H$ NMR is consistent with the structure.

EXAMPLE 1 STEP 2

Preparation of
2-bromo-4,5-dimethyl-3-thiophenecarboxylic acid,
ethyl ester

| Chemicals | Mol. Wt | Weight | Volume | Moles |
| --- | --- | --- | --- | --- |
| Step 1 Product | 199.00 | 300 g | — | 1.508 |
| t-Butyl nitrite | 103.12 | 251 g | 290 mL | 2.44 |
| Copper (II) bromide | 223.36 | 336 g | — | 1.504 |
| Acetonitrile | 41.05 | | 3 Liters, total | |

Step 1 product (300 grams of ethyl 2-amino-4,5-dimethyl-3-thiophenecarboxylate) is weighed out into a beaker. The solid is dissolved in 1.5 liters of dry acetonitrile with slight warming (25° C.). Any insolubles, if present, are filtered off. The solution in placed in an addition funnel set on the 5 L flask fitted with a bubbler and $N_2$ inlet setup.

Under an $N_2$ purge in a clean, dry 5 L RB flask, is placed 1.5 liters of dry acetonitrile. To this is added 336 grams of solid cupric bromide with stirring. After 5 minutes stirring to dissolve the copper bromide, 290 mLs of t-butyl nitrite is added and then the pot is heated to 30° C. When the temperature is reached, the nitrogen purge is closed and the thiophenecarboxylate solution is added dropwise over 30 minutes into the stirring flask, allowing the exotherm to carry the batch temperature to about 50° C. The batch will offgas as observed through the bubbler. After the addition is completed, the batch temperature is raised to 65°–70° C. and held for 45 minutes or until offgassing is nearly stopped. Heat is applied longer if offgassing is still ongoing.

When the reaction is finished, the contents of the 5 L flask are poured into a 12 L flask containing 3 liters of 5% HCl. One liter of ethyl acetate is added to the flask with vigorous agitation. The contents are stirred for 2–4 minutes and then the organic layer is separated. The contents are washed with distilled water, 500 mLs×2, then washed once with saturated brine, and then dried with $Na_2SO_4$. The ethyl acetate solution is decanted off the sodium sulfate and washed with few mLs of fresh solvent. The ethyl acetate solutions are added together and the solvent is rotovapped off at up to about 50° C. and 27" Hg vacuum. The yield is about 310–330 grams of a dark brown oily liquid. The dark brown oil is then Kugelrohr distilled at 96°–98° C. and 0.4 Torr to give around 200–220 grams of a white to pale yellow refractive oil. $^1$H NMR shows a product that contains a few % of the 5-H thiophene along with the bromothiophene product. Estimated yield is 55%.

EXAMPLE 1 STEP 3

Preparation of
2-bromo-4,5-dimethyl-3-thiophenecarboxylic acid

| Chemicals | Mol. Wt | Weight | Volume | Moles |
|---|---|---|---|---|
| Step 2 Product | 263 | 300 g | — | 1.14 |
| Sodium hydroxide | 40 | 91 g | | 2.28 |
| Ethanol | 46 | | 1 Liter | |

Step 2 product (300 grams of ethyl 2-bromo-4,5-dimethyl-3-thiophenecarboxylate) is poured into a 5 L flask fitted with a bubbler and $N_2$ inlet setup. One liter of ethanol is added with stirring to the flask. Sodium hydroxide pellets (91 g) are added to the stirring ester solution. The pale yellow solution darkens to orange brown. The batch is heated to 65°–70° C. and after about 1 hour, the batch is sampled and run on TLC (20% EtOAc/hexanes). When the disappearance of starting material is confirmed, the heating is stopped and the batch is transferred to a rotovap where the solvent is removed to dryness.

A liter of distilled water is added back to the batch to dissolve the carboxylic acid salt. The orange solution is washed with 100 mls×2 of ether. The aqueous layer is then separated and acidified with concentrated HCl. The slurry of free carboxylic acid is then stirred for 1–2 hours. Finally the solid is filtered, washed on the filter with 2×250 mls of 1% HCl and dried on the filter until powdery. The material is then placed in a vacuum oven at about 60° C. and 25" Hg vacuum for several hours to dry.

Product is obtained as a fine yellowish solid, mp 167°–73° C. A total of 225 g of 2-bromo-4,5-dimethyl-3-thiophenecarboxylic acid is isolated for ~85% yield. $^1$H NMR agrees with structure and also shows the 2–3% of the 5-H thiophene analog that is carded along.

EXAMPLE 1 STEP 4

Preparation of
2-trimethylsilyl-4,5-dimethyl-3-thiophenecarboxylic acid

| Chemicals | Mol. Wt | Amount (wt/vol) | Moles |
|---|---|---|---|
| Step 3 product | 235 | 100.0 grams | 0.426 |
| n-BuLi, 2.5 M in Hexane | 62 | 400 mLs | 1.00 (1.065) |
| Trimethylsilyl Chloride | 108.64 | 119.5 g/ 140 mLs | 1.10 |
| Tetrahydrofuran, anhyd. | 72.11 | 1.0 liter | |

Step 3 product (100 grams of 2-bromo-4,5-dimethyl-3-thiophenecarboxylic acid) is dissolved in 1 liter of anhydrous THF in a nitrogen swept dry 3 L RB flask fitted with a 1 liter addition funnel. The solution is cooled to −70° C. in a dry ice/isopropanol slush, maintaining the $N_2$ sweep. 400 mLs of 2.5 Molar n-butyllithium in hexane is transferred into the 1 liter addition funnel and the solution is run into the stirring batch keeping the temperature below −15° C. (−25° to −15°, average −20° C.).

After addition, the batch is cooled back to −30° to −40° C. and stirred in the cold for 45 minutes to 1 hour. Then 119.5 g (140 mLs) of trimethylsilyl chloride is added at −30° to −40° C. and stirring is continued for 45 minutes in the cold. After that time, the batch is warmed to 0° C. and poured into ice water (2 liters). The aqueous layer is separated and extracted with 500 mLs of methylene chloride. The methylene chloride layer is combined with the original organic layer (THF, hexane) and washed with saturated brine, dried ($Na_2SO_4$), and rotovapped to give 2-trimethylsilyl-4,5-dimethyl-3-thiophenecarboxylic acid in >95% yield: est. weight is 92+ grams. $^1$H NMR shows 97–100% TMS incorporation and no 5-H thiophene.

EXAMPLE 1 STEP 5

Acid to Add chloride to Amide

| Chemicals | Mol. Wt | Amount (wt/vol) | Moles |
|---|---|---|---|
| Step 4 product | 228 | 150 g | 0.658 moles |
| Oxalyl Chloride | 129.93 | 85.5 g | 0.658 moles |
| Methylene Chloride | | 750 mLs | |
| Dimethylformamide | | 5–10 drops to catalyze | |
| Allylamine | 57.10 | 86.5 g | 1.51 moles |

Step 4 product (150 grams of 2-trimethylsilyl-4,5-dimethyl-3-thiophenecarboxylic acid) is dissolved in 750 mLs of methylene chloride in a nitrogen swept 3 L RB flask and the batch is cooled to about 0° C. Oxalyl chloride (85.5 grams, 0.658 moles) is placed in an addition funnel and added dropwise to the stirring batch keeping the temperature under 10° C. and monitoring and controlling the offgasses venting through the bubbler ($N_2$ sweep is turned off when addition is started). When the addition is complete, the batch is stirred at ambient temperature for 30 minutes while monitoring offgassing. When no more offgas is seen, the batch is again swept with nitrogen and stirred vigorously for 15–30 minutes. Then the batch is rotovapped free of solvent and the acid chloride held under nitrogen. The acid chloride (a purplish oil) is diluted with 400 mLs of methylene chloride and transferred to the RB flask swept with $N_2$ and in a salt/ice bath for cooling. The batch is cooled to −10° C. for addition. Allylamine (86.5 g, 1.51 moles in 100 mls CH$_2$Cl$_2$) is added dropwise or in a stream at a rate that keeps the batch temperature below 10° C. When all of the amine is added, the batch is removed from the icewater bath, stirred at ambient for 1 hour and then sampled for $^1$H NMR. NMR shows compound I is formed. NMR will also disclose any desilylated byproducts (usually 10–20%). Solvent is removed from the batch on a rotary evaporator to give a red brown waxy semisolid. This material is treated with an equal volume of hexane to give a brown solution which is filtered to remove any insoluble material. Chilling the hexane solution to −15° to −25° C. crystallizes the product. The product slurry is stirred and then filtered cold to give the product ultimately as a tan felt-like solid from the waxy reddish solid originally isolated. Considerable effort is needed to clean up the crude product. Several crops can be isolated with increasing difficulty. From an estimated 160 grams of waxy semisolids, 67 grams of compound I of 96.4% area % by GC were isolated. Yield is 38%.

Alternatively, Compound I can be prepared as shown below in Example 2 using following methods and materials.

EXAMPLE 2 STEP 1

| Chemicals | MW | Weight | Volume | Moles |
|---|---|---|---|---|
| Example 1 Step 1 Product | 199 | 300 g | — | 1.508 |
| t-Butyl nitrite | 103.12 | 251.4 g | 290 mL | 2.44 |
| Copper-bronze | 63.54 | 9.5 g | — | 0.15 |
| Tetrahydrofuran | 72.11 | | 3 Liters, total | |

Example 1 Step 1 product (300 grams of ethyl 2-amino-4,5-dimethyl-3-thiophenecarboxylate) is weighed out into a beaker. The solid is dissolved in 1.5 liters of dry tetrahydrofuran. The solution is placed in an addition funnel set on the 5 L flask fitted with a bubbler and N$_2$ inlet setup.

Under an N$_2$ purge in a clean, dry 5 L RB flask, is placed 1.5 liters of dry tetrahydrofuran. To this is added 9.5 grams of copper-bronze with stirring. 290 mLs of t-butyl nitrite is added and then the pot is cooled to >0° C. When temperature is reached, the nitrogen purge is closed and the thiophenecarboxylate solution is started dropwise into the stirring flask, keeping the batch temperature to −0°–5° C. The batch will offgas as observed through the bubbler. After addition is completed, the batch is held for 45 minutes or until offgassing is nearly stopped at this time. Heat longer if offgassing is still ongoing.

When the reaction is finished, the contents of the 5 L flask are poured into a 12 L flask containing 3 liters of 5% HCl. One liter of ethyl acetate is added to the flask with vigorous agitation. The reaction is stirred for 2–4 minutes and then the organic layer is separated. The material is washed with DI water (500 mLs×2) then once with saturated brine, then dried with Na$_2$SO$_4$. The ethyl acetate solution is decanted off the sodium sulfate and is washed with a few mLs of fresh solvent. The ethyl acetate solutions are added together and the solvent is rotovapped off at up to 50° C. and 27" Hg vacuum. Yield is about 270 grams of a light brown liquid. The brown oil is then Kugelrohr distilled at 96°–98° C. and 0.4 Torr to give around 170 grams of a white to pale yellow refractive oil. $^1$H NMR shows a product that contains 100% of the 5-H thiophene as the product. Estimated yield is 60%. The product of this reaction, 2-protio-4,5-dimethyl-3-thiophenecarboxylic acid, ethyl ester, is used in the next step described below.

EXAMPLE 2

Step 2

To a solution of diisopropylamine (3.6 g, 36 mmol) in 30 mL of tetrahydrofuran at −30° C. is added under a positive atmosphere of nitrogen 15 mL of 2.5N n-butyllithium in hexane and stirred at between −20° and −30° C. for 0.5 h. A solution of 2-protio-4,5-dimethyl-3-thiophene carboxylic add (1.9 g, 12 mmol) in 20 mL of tetrahydrofuran is then added at −30° C. and the reaction mixture is stirred at −10° and −15° C. (with an ice-water-salt cooling bath) for 3 h. Chlorotrimethylsilane (5 mL, 40 mmol) is added and stirring is continued at between −10° and 0° C. for 3 h. After that, the mixture is poured into ice-water, acidified with 10 mL of concentrated hydrochloric acid, and extracted with methylene chloride (2×50 mL). The combined organic layers are washed with brine, dried (over MgSO$_4$) and concentrated in vacuo to give 2-(trimethylsilyl)-4,5-dimethyl-3-thiophenecarboxylic acid (2.4 g, 87.6% yield) as a brownish solid. This material is the same as Example 1 Step 4 product listed previously.

EXAMPLE 2 STEP 3

| Chemicals | Mol. Wt | Amount (wt/vol) | Moles |
|---|---|---|---|
| Example 1 Step 4 product | 228 | 32.4 g | 0.15 moles |
| Oxalyl Chloride | 127 | 21.0 g | 0.165 moles |
| Toluene | | 500 mLs | |
| Dimethylformamide | | 5–10 drops to catalyze | |
| Allylamine | 57.10 | 19.0 g | 0.33 moles |

Example 1 Step 4 product (32.4 grams of 2-trimethylsilyl-4,5-dimethyl-3-thiophenecarboxylic acid) is dissolved in 500 mLs of toluene in a nitrogen blanketed 1 L RB flask and the batch is cooled to about 0° C. Oxalyl chloride (21.0 grams, 0.165 moles) is placed in an addition funnel and added dropwise to the stirring batch keeping the temperature under 10° C. and monitoring and controlling the offgasses venting through the bubbler. A nitrogen sparge of the reaction mixture is maintained in order to remove HCl. When the addition is complete, the batch is stirred at ambient temperature for 3 hrs while monitoring by GC. When the reaction is finished, the batch is rotovapped free of any residual oxalyl chloride by removing about 100 ml of toluene. The acid chloride solution is transferred to the RB flask swept with N$_2$ and placed in a salt/ice bath for cooling. The batch is cooled to 15° C. for addition. Allylamine (19.0 g, 0.33 moles in 50 ml toluene) is added dropwise or in a stream at a rate that keeps the batch temperature below 35° C. When all of the amine is added, the batch is removed from the icewater bath, stirred at ambient for 1 hour and then sampled for GC which shows formation of compound I is completed. At that time, the toluene mixture is washed with about 500 ml of water and the solvent removed to yield 38.3 g of compound I as a solid as determined by NMR and GC/MS.

Compositions

Control of Gg diseases, including Take-All, using a chemical control agent may be accomplished in several ways. The agent may be applied directly to soft infested with Gg, for example, at the time of planting along with the seed. Alternatively, it may be applied to the soil after planting and germination. Compositions for soil application include clay granules which may be applied in-furrow, as broadcast granules or as impregnated fertilizer granules. In addition, the agent may be applied to the soil as a preemergent or postemergent spray.

Preferably, however, the agent is applied to the seed in a coating prior to planting. This technique is commonly used in many crops to provide fungicides for control of various phytopathological fungi.

Compositions of the present invention are comprised of a fungicidally effective amount of compound I described above and one or more adjuvants. The active ingredient may be present in such compositions at levels from 0.01 to 95 percent by weight. Other fungicides may also be included to provide a broader spectrum of fungal control. The choice of fungicides will depend on the crop and the diseases known to be a threat to that crop in the location of interest.

The fungicidal compositions of this invention, including concentrates which require dilution prior to application, may contain at least one active ingredient and an adjuvant in liquid or solid form. The compositions are prepared by admixing the active ingredient with or without an adjuvant plus diluents, extenders, carriers, and conditioning agents to provide compositions in the form of finely-divided particulate solids, granules, pellets, solutions, dispersions or emulsions. Thus, it is believed the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, block copolymers, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred disper-sants are methyl, cellulose, polyvinyl alcohol, sodium lignin sulfonates, polymeric alkyl naphthalene sulfonates, sodium naphthalene sulfonate, polymethylene bisnaphthalene sulfonate, and neutralized polyoxyethylated derivatives or ring-substituted alkyl phenol phosphates. Stabilizers may also be used to produce stable emulsions, such as magnesium aluminum silicate and xanthan gum.

Other formulations include dust concentrates comprising from 0.1 to 60% by weight of the active ingredient on a suitable extender, optionally including other adjuvants to improve handling properties, e.g., graphite. These dusts may be diluted for application at concentrations within the range of from about 0.1–10% by weight.

Concentrates may also be aqueous emulsions, prepared by stirring a nonaqueous solution of a water insoluble active ingredient and an emulsification agent with water until uniform and then homogenizing to give stable emulsion of very finely-divided particles. Or they may be aqueous suspensions, prepared by milling a mixture of a water-insoluble active ingredient and wetting agents to give a suspension, characterized by its extremely small particle size, so that when diluted, coverage is very uniform. Suitable concentrations of these formulations contain from about 0.1–60% preferably 5–50% by weight of active ingredient.

Concentrates may be solutions of active ingredient in suitable solvents together with a surface active agent. Suitable solvents for the active ingredients of this invention for use in seed treatment include propylene glycol, furfuryl alcohol, other alcohols or glycols, and other solvents which do not substantially interfere with seed germination. If the active ingredient is to be applied to the soil, then solvents such as N,N-dimethylformamide, dimethylsulfoxide, N-methylpyrrolidone, hydrocarbons, and water immiscible ethers, esters, or ketones are useful.

The concentrate compositions herein generally contain from about 1.0 to 95 parts (preferably 5–60 parts) active ingredient, about 0.25 to 50 parts (preferably 1–25 parts) surface active agent and where required about 4 to 94 parts solvent, all parts being by weight based on the total weight of the concentrate.

The following 125 g/l a.i. suspension concentrate of compound I may be utilized in accordance with the present invention.

| Ingredient | Amount g/L |
|---|---|
| 4,5-dimethyl-N-2-propenyl-2-(trimethylsilyl)-3-thiophene carboxamide (96%) (Cmpd I) | 130.4 |
| Pluronic PE 10500 | 40.0 |
| Polypropylene glycol | 80.0 |
| Polyfon O | 10.0 |
| Permanent Rubine LB6 02 | 30.0 |
| Rhodorsil 432R | 1.0 |
| Orchex 796 | 40.0 |
| Vinamul 18160 | 60.0 |
| Rhodopol 23 | 0.80 |
| Phylatol | 0.32 |
| Water | 641.9 |
| Specific gravity = 1.034 | |

In addition, the following 250 g/l a.i. suspension concentrate of compound I may be utilized in accordance with the present invention.

| Ingredient | Amount g/L |
|---|---|
| 4,5-dimethyl-N-2-propenyl-2-(trimethylsilyl)-3-thiophene carboxamide (Cmpd I) | 275.5 |
| Pluronic PE 10500 | 35.2 |
| Polypropylene glycol | 71.5 |
| Polyfon O | 10.7 |
| Permanent Rubine LB6 02 | 21.4 |
| Rhodorsil 432R | 0.85 |
| Orchex 796 | 61.9 |
| Vinamul 18160 | 64.1 |
| Rhodopol 23 | 0.75 |
| Panacide M | 0.75 |
| Water | 525.4 |
| Specific gravity = 1.068 (estimated) | |

For application to the soil at the time of planting, a granular formulation may be used. Granules are physically stable particulate compositions comprising at least one active ingredient adhered to or distributed through a basic matrix of an inert, finely divided particulate extender. In order to aid leaching of the active ingredient from the particulate, a surface active agent such as those listed hereinbefore, or for example, propylene glycol, can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the fungicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The method of the present invention may be carried out by mixing the composition comprising the active ingredient into the seed prior to planting at rates from 0.01 to 50 g per kg of seed, preferably from 0.1 to 5 g per kg, and more preferably from 0.2 to 2 g per kg. If application to the soil is desired, the compounds may be applied at rates from 1 to 1000 g per hectare, preferably from 10 to 500 g per hectare. The higher application rates will be needed for situations of light soils or greater rainfall or both.

Biological Assays

Compound I of the present invention was tested for fungicidal effectiveness and has demonstrated control of Gg as shown in the following tests. The tests are generally listed in the order of increasing refinement, i.e. each succeeding test better defines the utility of the test compound to control of the growth of Gg. The earlier tests were conducted to identify compounds active against Gt. The later listed tests were conducted to characterize the fungicidal activity, i.e. define unit activity on whole wheat plants. The fungicidal data are shown below.

In vitro Assay

Compound I (0.25 mL of an appropriate stock solution in acetone) is incorporated into 25 mL minimal media agar and plates are prepared. The minimal media agar is prepared by autoclaving a solution of 17.5 g Czapek Dox broth (Difco), 7.5 g purified agar or Bacto-agar (Difco), and 500 mL distilled/deionized water, and then adding 50 μL of 1 mg/mL thiamine hydrochloride and 50 μL of 1 mg/mL biotin in 5% ethanol. Each plate is inoculated by placing in a triangular shape three 4-mm plugs of *Gaeumannomyces graminis* var. tritici (Ggt) grown on the minimal media agar described above. The plates are incubated in the dark at 19°–20° C. for 4 to 5 days. The growth of the fungus is measured as the diameter of the mycelial growth. The result is expressed as Percent Inhibition, calculated as [1-[(mm growth on treated plate-4)/(mm growth on control plate-4)]]×100. The results of these tests are as follows:

| Rate | Percent Inhibition | | |
|---|---|---|---|
| ppm | Test 1 | Test 2 | Test 3 |
| control | 0 | 0 | 0 |
| 10.0 | 100 | | |
| 1.0 | 100 | 98 | |
| 0.1 | 98 | 98 | |
| 0.01 | | 98 | 97 |
| 0.001 | | 93 | 97 |
| 0.0001 | | | 59 |
| 0.00001 | | | 3 |

In vivo Test-4 Week Seed Treatment Assay

Compound I was tested for control of Ggt on 'Bergen' varieties of wheat grown in 3-inch square pots containing soil (equal to thirds of Metro-mix, sand, and silt-loam field soil, all steam sterilized). Seeds are treated with a solution of compound I of the present invention in acetone. Using a 10,000 ppm stock for each compound the following serial dilutions are prepared:

| Solution Number | Solution ppm | gm/kg of seed when 1 mL is applied to 10 gm of seed |
|---|---|---|
| 1 | 10,000 | 1.0 |
| 2 | 5,000 | 0.5 |
| 3 | 2,500 | 0.25 |
| 4 | 1,250 | 0.125 |
| 5 | 625 | 0.0625 |

When 1 mL of the stock and dilutions is applied to 10 gm of seed, the resultant applications rates are 1.0, 0.5, 0.25, 0.125 and 0.0625 g/kg of seed. Solution 5 is optional and not used in all tests.

A treatment jar is rinsed 2 times with 3 ml of acetone. The 1 ml of the solution is swirled to cover the base of the jar. 10 g of seed are added to the jar and capped after which the jar is swirled and shaken until the seeds get a rapid and even coverage. After about 30–50 seconds the lid is removed as the shaking is continued. After 1 minute the jar is set down to dry. When dry, the seed are poured back into the envelope for either planting in the pots or stored until such planting.

Compounds are tested for control of Ggt on 'Bergen' varieties of wheat grown in 3-inch square pots containing soil infested with Ggt. The infestation is accomplished by mixing the soil with an inoculum prepared by growing Ggt on infested sterile oats (400 cc whole oats, 350 mL deionized water, autoclaved). After a one-month incubation period at room temperature, the oats are dried and mixed with the soil at 4% v/v.

The roots are harvested, washed, and rated after 4 weeks. Each treatment is assigned a percent (%) diseased root area values using 1, 5, 10, 20, 30, 40, 50, 60, 80, or 100% ratings. Each pot of plants gets a single rating. The results of these tests are as follows.

| | Rate g a.i./ | % Disease Control | | |
|---|---|---|---|---|
| Cmpd | kg seed | Test 1 | Test 2 | Test 3 |
| Control | 0 | 0 | 0 | 0 |
| I | 1.0 | 97 | | |
| I | 0.5 | 91 | 100 | |
| I | 0.25 | 93 | 99 | 96 |
| I | 0.125 | 97 | 86 | 95 |

In Vivo Assay-4 weeks

Compound I was tested for control of Ggt on 'Bergen' varieties of wheat grown in 3-inch square pots containing soil infested with Ggt. The infestation is accomplished by mixing the soil with an inoculum prepared by growing Ggt on ¼ strength potato dextrose agar (4.875 g potato dextrose agar, 5.0 g Bacto agar, 500 mL distilled, deionized water) in plates and using plugs from the plates to infest sterile oats (400 cc whole oats, 350 mL deionized water, autoclaved). After a one-month incubation period at room temperature, the oats are dried and mixed with the soil at 4% v/v. The pots are filled with soil to about one cm from the top of the pot. Four wheat seeds are placed on top of the soil in each pot. The test compounds are prepared as an 1:9 acetone/water v/v solution containing 0.18% Tween® 20 to provide a treatment rate of 0.5 and/or 0.1 mg active ingredient per pot, treated with 3 mL test solution per pot. Five pots are used for each treatment level and the controls, which are untreated, inoculated and non-inoculated pots. After one hour drying time, the seeds are covered with more of the appropriate infested soil. The pots are placed in a growth chamber and watered each day. After four weeks, each pot is evaluated for evidence of disease by examination of the sequinal roots of each plant under a dissecting microscope. A zero to 5 rating scale having the following meanings is used:

0=no runner hyphae or lesions present

1=runner hyphae and a few small lesions present on <10% of root system

2=runner hyphae and small lesions present on 10–25% of root system

3=runner hyphae and lesions present on 25–50% of root system

4=runner hyphae and many, large, coalescing lesions on >50% of root system

5=root system and culm completely inundated with lesions and runner hyphae

From each set of five replicates a high or low score may be eliminated to assure the best representative scores are used to calculate a replicate mean by averaging the remaining scores. This mean score is then compared to the untreated control score and a percent disease control is calculated. The results of these in vivo tests are reported in the Table below.

| Cmpd | Rate mg/pot | % Disease Control | |
|---|---|---|---|
| | | Test 1 | Test 2 |
| Control | 0.0 | 0 | 0 |
| I | 0.5 | 100 | |
| I | 0.1 | 100 | 100 |
| I | 0.02 | 100 | 95 |
| I | 0.004 | | 92 |

In vivo Test-8 week Seed Treatment Assay

Compound I was tested for control of Ggt on 'Bergen' varieties of wheat grown in 6-inch round pots containing soil (equal to thirds of Metro-mix, sand, and silt-loam field soil, all steam sterilized). Seeds are treated with a solution of compound I of the present invention at 10,000 ppm stock solution in acetone. Using a 10,000 ppm stock for each compound the following serial dilutions are prepared:

| Solution Number | Solution ppm | gm/kg of seed when 1 mL is applied to 10 gm of seed |
|---|---|---|
| 1 | 10,000 | 1.0 |
| 2 | 5,000 | 0.5 |
| 3 | 2,500 | 0.25 |
| 4 | 1,250 | 0.125 |

When 1 mL of the stock and dilutions is applied to 10 gm of seed, the resultant applications rates are 1, 0.5, 0.25 and 0.125 g/kg of seed.

A treatment jar is rinsed 2 times with 3 ml of acetone. The 1 ml of the solution is swirled to cover the base of the jar. 10 g of seed are added to the jar and capped after which the jar is swirled and shaken until the seeds get a rapid and even coverage. After about 30–50 seconds the lid is removed as the shaking is continued. After 1 minute the jar is set down to dry. When dry, the seed are poured back into the envelope for either planting in the pots or stored until such planting.

The method of planting is as follows. The 6-inch pots are packed to their ledge with the above soil mix. Treated seed is placed on the surface of soil (packed to ledge) 8 seeds per pot with the seeds about 2–3 inches apart. There are 5 pots (replicates) planted per treatment. 15 ml of oat inoculum prepared as previously described (about 4 g) is measured and sprinkled evenly over the soil surface of each pot. The soil/seed/inoculum is covered with 180 ml of soil mix (same as above). A 150 ml beaker filled to the top edge is about 180 ml. This water is used to initially water lightly several times to wet soil without washing out seeds.

In cool winter months the pots are placed in a greenhouse at 16°–18° C. with only minimal supplemental light. In warmer months the pots are placed in a growth chamber set at 17° C. for 3–4 weeks to establish disease, then placed in greenhouse until harvest. The roots are harvested, washed, and rated after 7–10 weeks. Each treatment is assigned a percent (%) diseased root area values using 1, 5, 10, 20, 30, 40, 50, 60, 80, or 100% ratings. Each pot of plants gets a single rating. The results of these tests are as follows:

| Cmpd | Rate g a.i./ kg seed | % Disease Control | |
|---|---|---|---|
| | | Test 1 | Test 2 |
| Control | 0 | 0 | 0 |
| I | 1.0 | 100 | 99 |
| I | 0.5 | 98 | 98 |
| I | 0.25 | 90 | 92 |
| I | 0.125 | 80 | 91 |

Field Tests-Spring Wheat Trials

Compound I was evaluated in two wheat field trials. Field plots (1.1 m×8 m) were planted with spring wheat (variety Minaret) at a seeding rate of 180 kg/ha. Compound I was applied in acetone at 25 and 100 g a.i./100 kg seed. Root infections by Take-All disease were assessed by washing the roots clean of soil. The roots were then placed under water against a white background and were rated according to the following scale:

| Root Rating Scale | Category |
|---|---|
| 0% root infection (heathy roots) | 0 |
| 1–10% roots infected | 1 |
| 11–25% roots infected | 2 |
| 26–50% roots infected | 3 |
| 51–75% roots infected | 4 |
| 76–100% roots infected | 5 |

A Take-All index of 0–100 is calculated based on the following formula:

$$\text{Take-All Index } (TAI) = \frac{100(b + 2c + 3d + 4e + 5f)}{5t}$$

where a, b, c, d, e, and f represent the number of plants in each category and t is the total number of plants assessed. A high TAI value indicates high Take-All infection. Growth Stage 30–31 represents the first node stage, Growth Stage>69 represents the end of flowering. Yield is expressed in tons/ha. Data for these trials are as follows:

Spring Wheat Field Trial 1

| Treatment | g ai/100 kg seed | TAI at Stage 30–31 1st node | TAI at Stage > 69 end of flowering | Yield T/ha |
|---|---|---|---|---|
| Control | 0 | 9.6 | 25.8 | 5.59 |
| Compound I | 25 | 4.9 | 15.7 | 5.96 |
| Compound I | 100 | 3.1 | 12.3 | 5.48 |

Spring Wheat Field Trial 2

| Treatment | g ai/100 kg seed | TAI at Stage 30–31 1st node | TAI at Stage > 69 end of flowering | Yield T/ha |
|---|---|---|---|---|
| Control | 0 | 7.3 | 28.5 | 6.49 |
| Compound I | 25 | 4.5 | 18.8 | 6.24 |
| Compound I | 100 | 3.9 | 11.1 | 6.36 |

Dry weather conditions limited the severity of Take-All disease in these spring sown trials. The disease level was fairly low and was not severe enough to cause whitehead development. In addition there was little impact on yield.

Field Tests-Winter Wheat Trials

Compound I was evaluated in seven winter wheat trials. The variety varied by location and was either Riband, Forby or Rossini. Compound I was formulated as described above and applied as a seed treatment at a single rate of 25 g a.i/100 kg seed. All plots were sown at a rate of 160 kg/ha. The level of root infection due to Take-All was assessed at growth stage 69 (end of flowering) according to the scale outlined above, and the take-all index (TAI) was calculated. A high level of Take-All developed in four of the seven trials, and the incidence of whiteheads (sterile or shriveled seed heads resulting from severe root infection) were assessed in three of these. Grain yield also was measured in the same three trials. The three remaining trials had lower levels of Take-All. Whiteheads did not develop in these lower disease trials, and the disease was not severe enough to impact yield.

Means from Four High-level of Disease Winter Wheat Trials

| | | Three trials only | | |
|---|---|---|---|---|
| Treatment | g a.i./100 kg seed | TAI | % Whiteheads | Yield (T/ha) |
| Control | 0 | 44.0 | 33.4 | 7.02 |
| Compound I | 25 | 30.0 | 16.1 | 8.33 |

Means from Three Trials Low-level of Disease Winter Wheat Trials

| | | Three trials only | | |
|---|---|---|---|---|
| Treatment | g a.i./100 kg seed | TAI | Whiteheads | Yield (T/ha) |
| Control | 0 | 26.5 | not developed | 9.51 |
| Compound I | 25 | 16.2 | not developed | 9.46 |

From the foregoing, it will be seen that this invention is one well adapted to attain all the ends and objects hereinabove set forth together with advantages which are obvious and which are inherent to the invention.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth is to be interpreted as illustrative and not in a limiting sense.

We claim:

1. A compound which is 4,5-dimethyl-N-2-propenyl-2-trimethylsilyl)-3-thiophenecarboxamide.

2. A fungicidal composition comprising a fungicidally effective amount of the compound of claim 1 in an agronomically acceptable carrier.

3. A composition of claim 2 in which the composition is a suspension concentrate.

4. A method of controlling disease in a plant caused by Gaeumannomyces species which comprises applying an effective amount of the compound in claim 1.

5. A method of claim 4 in which the application is to a plant locus.

6. A method of claim 5 in which the application is to plant seed.

7. A method of claim 4 in which the application is to the soil.

\* \* \* \* \*